United States Patent [19]

Silver et al.

[11] Patent Number: 4,900,553
[45] Date of Patent: Feb. 13, 1990

[54] METHOD OF REDUCING GLIAL SCAR FORMATION AND PROMOTING AXON AND BLOOD VESSEL GROWTH AND/OR REGENERATION THROUGH THE USE OF ACTIVATED IMMATURE ASTROCYTES

[75] Inventors: Jerry Silver, Lyndhurst; George M. Smith, Cleveland; James W. Jacobberger, Chesterland, all of Ohio

[73] Assignee: Case Western Reserve University, Cleveland, Ohio

[21] Appl. No.: 96,373

[22] Filed: Sep. 11, 1987

[51] Int. Cl.$^4$ ............................................. A61F 13/00
[52] U.S. Cl. ..................................... 424/422; 424/93; 424/423; 435/174; 435/176; 435/177; 435/240.1; 435/240.242; 435/240.243; 435/246; 435/240.241; 935/12
[58] Field of Search ................ 435/174, 176, 179, 177, 435/240.241, 240.242, 240.243, 240, 246; 935/12; 424/93, 422, 423

[56] References Cited

U.S. PATENT DOCUMENTS

| 4,376,071 | 3/1983 | Jennings et al. | 424/95 X |
|---|---|---|---|
| 4,378,344 | 3/1983 | Zahradnik et al. | 436/531 X |
| 4,388,309 | 6/1983 | Fabricius et al. | 424/85.2 |
| 4,532,134 | 7/1985 | Malette et al. | 424/95 X |
| 4,574,116 | 3/1986 | Kaplan et al. | 435/68 |
| 4,642,291 | 2/1987 | Cairncross et al. | 435/240 |
| 4,662,884 | 5/1987 | Stensaas et al. | 623/12 |
| 4,707,448 | 11/1987 | Major | 435/240.25 |

OTHER PUBLICATIONS

Campbell and Bassette, 1956, Surgical Forum 7:570-574.
Campbell et al., 1957, Science 126:929.
Bassett et al., 1959, Experimental Neurology 1:386-406.
Kalil and Reh, 1979, Science 205:1158-1161.
Silver and Robb, 1979, Dev. Biol. 68:175-190.
Kromer et al., 1980, Brain Res. 210:153-171.
David and Aguayo, 1981, Science 214:931-933.
Kromer et al., 1981, Brain Res., 210:173-200.
Lindsay et al., 1982, Brain Res. 243:329-343.
Silver et al., 1982, J. Comp. Neurol. 210:10-29.
Bottenstein and Sato, Proc. Natl. Acad. Sci. U.S.A. 79:514-517, (1983).
Labbe et al., 1983, Science 221:470-472.
Reier et al., 1983, in "Spinal Cord Reconstruction", Kao, Bunge, and Reier, eds., Raven Press, New York, pp. 163-195.
Silver and Ogawa, 1983, Science, 220:1067-1069.
Barrett et al., 1984, Exp. Neurol. 84:374-385.
Noble et al., 1984, J. Neurosci. 4:1892-1903.
Bernstein et al., 1985, Brain Res. 327:135-141.
Carlstedt, 1985, Brain Res. 347:188-191.
Fallon, 1985, J. Cell Biol. 100:198-207.
Freed et al., 1985, Science 227:1544-1552.
Friedman et al., 1985, J. Neurosci. 5:1616-1625.
Kromer and Cornbrooks, 1985, Proc. Natl. Acad. Sci. U.S.A. 82:6330-6334.
Mathewson et al., 1985, Brain Res. 327:61-69.
Kesslak et al., 1986, Exp. Neurology 92:377-390.
Manthorpe et al., 1986, in "Astrocytes" vol, 2, Federoff and Vernadakis, eds, Academic Press, New York, pp. 315-376.
Schelper et al., 1986, J. Neuropath. and Exper. Neurol. 45:1-19.
Smith et al., 1986, J. Comp. Neurol. 251:23-43, (1986).
Azimitia and Bjorklund, 1987, Annals of the New York Academy of Sciences 495:722-725.
Bunge, 1987, J. Exp. Biol. 132:21-34.
Liuzzi and Lasek, 1987, Science 237:642-645.
Yannas et al., 1987, in "Advances in Biomedical Polymers", Gebelein, ed., Plenum Publishing Corp., pp. 1-9.
Silver, 1988, Clin. Res. 36:196-199.

Primary Examiner—Thurman K. Page
Attorney, Agent, or Firm—Pennie & Edmonds

[57] ABSTRACT

The present invention relates to "activated" immature astrocytes and methods of utilizing the activated immature astrocytes to reduce secondary necrosis and scar formation in central nervous system tissue as well as to promote axon and/or blood vessel growth or regeneration. In specific embodiments of the invention, activated immature astrocytes are used in injectable form or on a polymer implant. The activated immature astrocytes and pharmaceutical compositions comprising same, may be used to treat disorders of the nervous system resulting from accidents or diseases which have in some way damaged the nerve tissue.

57 Claims, 20 Drawing Sheets

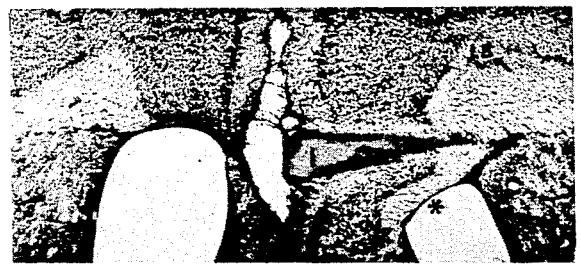
FIG.3a

FIG.3c
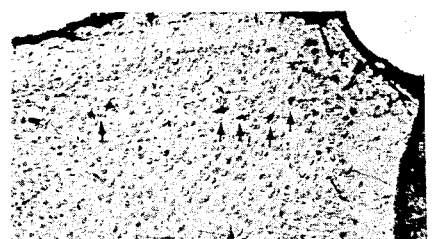 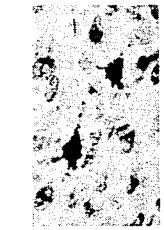
FIG.3d FIG.3e

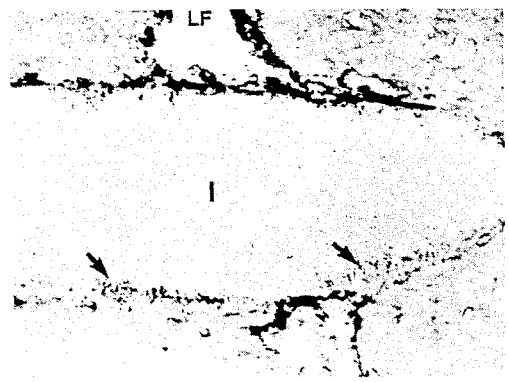
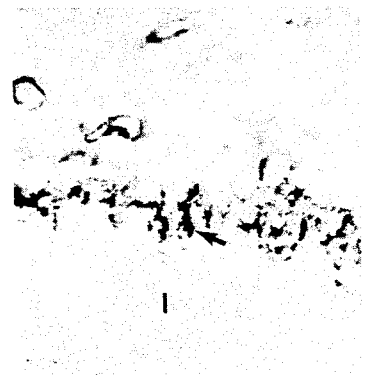
FIG.6a  FIG.6b
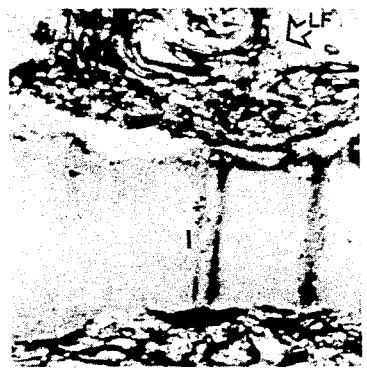
FIG.6c  FIG.6d
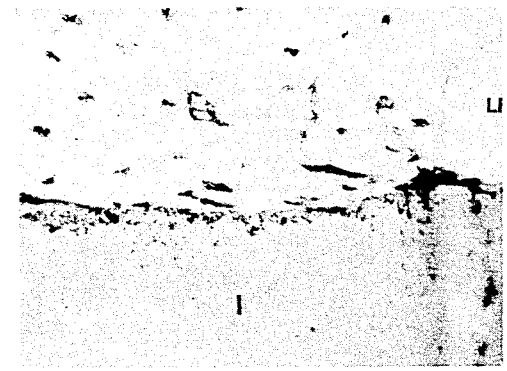
FIG.6e  FIG.6f

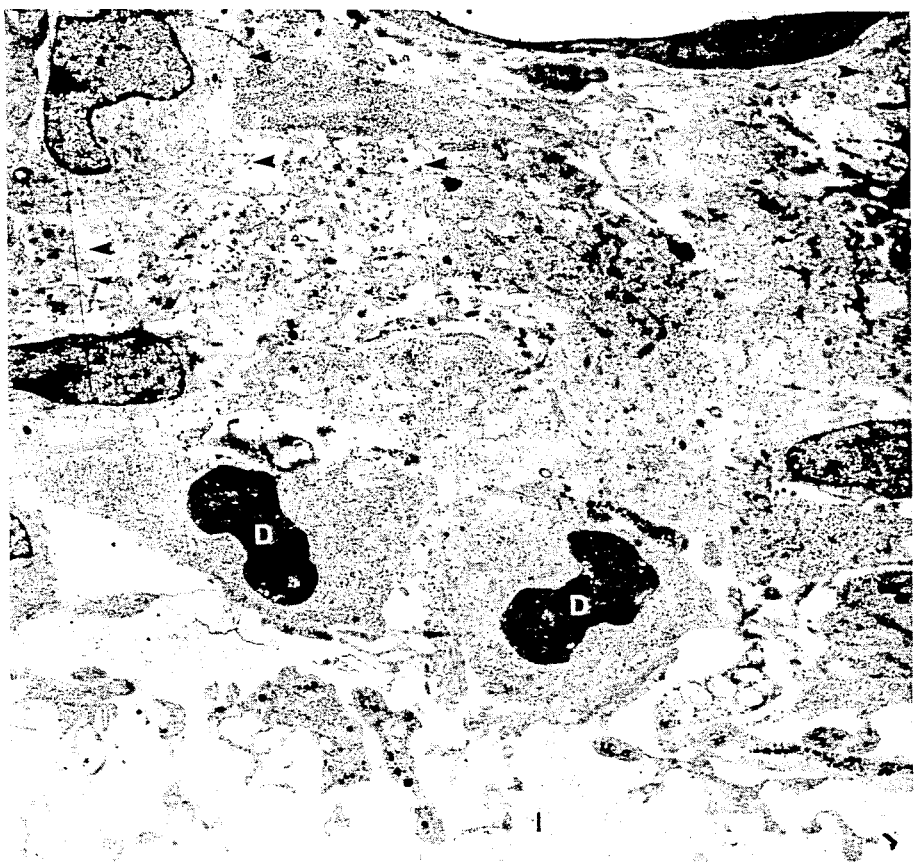
FIG.12a
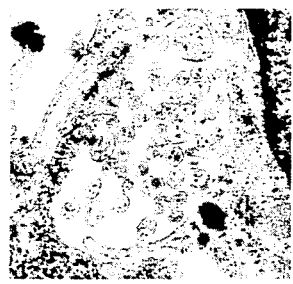
FIG.12b
FIG.12c
FIG.12d

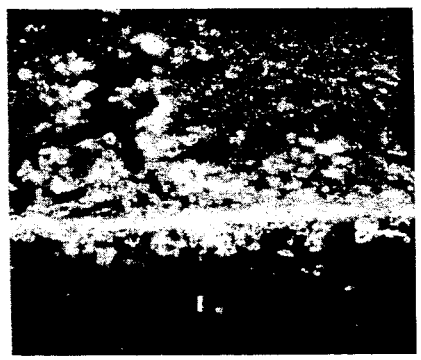
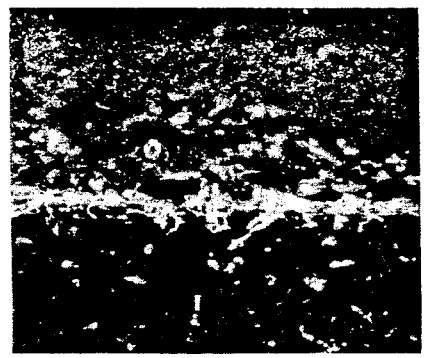
FIG.13a FIG.13b
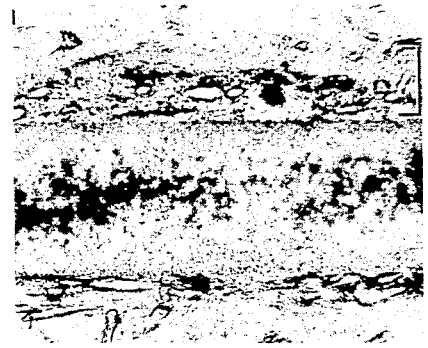
FIG.13c FIG.13d
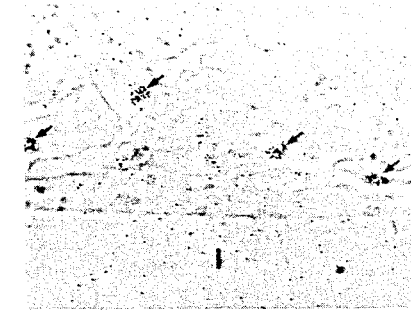
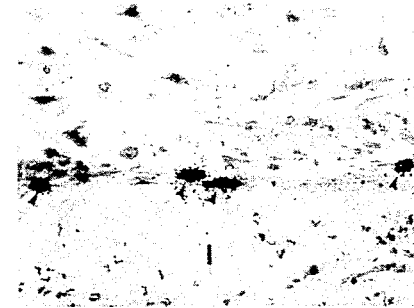
FIG.13e FIG.13f

METHOD OF REDUCING GLIAL SCAR FORMATION AND PROMOTING AXON AND BLOOD VESSEL GROWTH AND/OR REGENERATION THROUGH THE USE OF ACTIVATED IMMATURE ASTROCYTES

Pursuant to the provisions of 35 U.S.C. §202 (c), it is hereby acknowledged that the Government has certain rights in this invention, which was made in part with funds from the National Eye Institute of the National Institutes of Health.

BACKGROUND OF THE INVENTION

The present invention relates to "activated" immature astrocytes and the method of utilizing the activated immature astrocytes in injectable form or on nitrocellulose polymer as a means for reducing secondary necrosis and glial scar formation in lesions in the brain and spinal cord as well as promoting directed blood vessel and axon growth and/or regeneration. The activated immature astrocytes and pharmaceutical compositions comprising same, may be used to treat disorders of the nervous system resulting from accidents or diseases which have in some way damaged the nerve tissue.

In the central nervous system the chief non-nervous cells are the glial cell types. These vary in numbers and type from one part of the nervous system to another, but the two basic classes can be distinguished by their size and embryonic origin, namely the marcroglia, i.e. which are relatively large cells derived from the neural plate, and the smaller microglia which stem from the mesodermal tissues surrounding the nervous system.

The microglia comprise two cell types, the astrocytes (astroglial cells) and the oligodendrocytes (oligodendroglial cells). The present invention is directed to the use of the former, i.e. astroglial cells, in their immature "activated" state, to reduce both secondary cell death and glial scar formation and promote axon regeneration and blood vessel growth.

Astrocytes possess small cell bodies (the nucleus is about 8 mm in diameter in man) with ramifying dendrite-like extensions. The cytoplasmic processes of astrocytes carry fine, foliate extensions which partly engulf and separate neurons and their neurites, and often end in plate-like expansions on blood vessels, ependyma and on the pial surface of the central nervous system.

The functions of astrocytes are numerous. They act mechanically as a supporting component of the nervous system. Their microfilaments, microtubules, and surface contact zones fit them for this task. They also act defensively by phagocytosing foreign material or cell debris. They can function as antigen presenting cells to macrophages and can provide a means of limited repair by forming glial scar tissue or filling the gaps left by degenerated neurons. In addition, they have essential metabolic functions in regulating the biochemical environment of neurons, providing nutrients, and regulating acid-base levels, etc.

Moreover, the astrocytes, which are able to divide in immature and mature animals, pass after mitosis through a series of structural transformations depending on their state of maturity. In areas of brain injury in young or old animals they proliferate (gliosis) to produce neural support. In a penetrating injury to the central nervous system (CNS) of adult mammals, severe tissue damage and secondary necrosis occurs in the region surrounding the wound. The degenerating effects caused by the injury are believed to generate a response in the surviving glial cells adjacent to the site of the injury (Reier et al., *The Astrocytic Scar As an Impediment to Regeneration in the Central Nervous System*, Spinal Cord Reconstruction, Raven Press, N.Y. pp. 163-195, 1983). The astrocyte response consists of a slight mitotic increase, an increase in size (hypertrophy), and a concomitant increase in quantity of intermediate filaments (Mathewson, et al., *Observations on the Astrocyte Response to a Cerebral Stab Wound in Adult Rats*, Brain Res., 327: 61-69, 1985). Together with invading monocytes, the astrocytes act as phagocytes to clear debris within the wound cavity. (Schelper, et al., *Monocytes Become Macrophages: They do not become Microglia: A Light and Electron Microscopic Autoradiographic Study Using 125-Iododeoxyuridine*, J. Neuropath., and Exper. Neurol., 45: 1-19, 1986). When the injury disrupts the plial lining of the brain, fibroblasts migrate into the wound cavity and multiple layers of basal lamina form over the astrocyte surface (Bernstein, et al., *Astrocytes Secret Basal Lamina after Hemisection of the Rat Spinal Cord*, Brain Res., 327: 135-141, 1985). The fibroblasts also produce collagen, which forms dense bundles within the surrounding extracellular spaces several weeks after injury. Thus, in adults the astrocytes, together with other cellular elements, form dense interwoven scars which fill the space vacated by the dead or dying cells in the injury area. Although the scar may help save the organism it also blocks axonal regeneration and the individual is left with an irreversible functional deficit or epileptic focus depending on the site of the lesion.

One embodiment of the present invention relates to the use of "activated" immature astrocytes to reduce the glial scar formation produced as described above. Previous studies by the inventors and others indicated that penetrating lesions in the central nervous system (CNS) of neonatal mammals rarely resulted in the formation of glial scars similar to those observed in adults and that the production of typical adult glial scars after injury increased after the first two postnatal weeks in rodents. (Barrett, et al., *Differences Between Adult and Neonatal Rats in their Astroglial Response to Spinal Injury*, Exp. Neurol., 84: 374-385, 1948; and Smith, et al., *Changing Role of Forebrain Astrocytes During Development, Regenerative Failure, and Induced Regeneration Upon Transplantation*, J. Comp. Neurol. 251: 23—43, 1986).

Moreover, the inventors have recently discovered in young animals implanted in their cerebral cortices with cellulose filters before postnatal day 8 (P8), that astrocytes did not produce a scar around the implant but instead sent many processes into the pores of the filter "suturing" it into the CNS. In contrast, astrocytes in older mice (implanted on or later than postnatal day 14)failed to incorporate the filter within the brain and, instead, produced a glial-mesenchymal scar around the filter which, in turn, did not support axon growth. The age related changes in the CNS response to wounding and the incorporation of the implant indicated the presence of a critical period wherein "activated" immature astrocytes (postnatal day 8 or less) repressed scar formation and post-critical astrocytes (postnatal day 14 or greater) produced glial scars. One embodiment of the present invention is directed to this discovery of the "cell suturing" phenomenon, wherein activated immature astrocytes are transplanted on polymer or as an injected suspension from a critical period animal to a post-critical period animal to reduce glial scar formation.

An additional embodiment of the present invention relates to a method for utilizing activated immature astrocytes as a means for promoting directed axon regeneration. Previous studies have demonstrated that CNS axons have the potential to grow long distances through peripheral nerve grafts (Friedman, et al., *Injured Neurons in the Olfactory Bulb of the Adult Rat Grow Axons along Grafts of Peripheral Nerve*, J. Neurosci. 5: 1616–1625, 1985) or Schwaan cell bridges (Kromer, et al., *Transplantation of Schwaan Cell Cultures Promote Axonal Regeneration in the Adult Mammalian Brain*, Proc. Natl. Acad. Sci. 82: 6330–6334. 1985). However, the studies with peripheral nerve elements indicated that regenerating nerve fibers could only extend a short distance upon reentry into the CNS most likely due to the formation of scars at the ends of the graft. Thus, although the injured adult CNS is potentially capable of a considerable amount of regeneration, sprouting is usually abortive and the axons fail to reinnervate their appropriate targets.

In addition, studies by the inventors indicated that developing axons are guided by oriented "highways of astroglial tissues". (Silver, et al., *Studies on the Development of the Eye Cup and Optic Nerve in Normal Mice and Mutants with Congenital Optic Nerve Aplasia*, Dev. Biol. 68: 175–190, 1979; Silver et al., *Axonal Guidance During Development of the Great Cerebral Commissures: Descriptive and Experimental Studies, in Vivo, on the Role of Preformed Glial Pathways*, J. Comp. Neurol., 210: 10–29, 1982). In lesioned areas of the embryonic brain that lack guidance pathways the forming axon tracts gather into massive neuromas. Perhaps the most dramatic demonstration of such an axonal disorder was shown in rats having surgically induced acallosal malformations. When a glial bridge is lesioned embryonically all or most of the fibers of the largest axonal pathway in the mammalian brain, the corpus callosum, failed to cross into opposite cerebral hemispheres. These axons did not die. Instead, as the fibers arrived on schedule at the hemisphere midline, they gathered into massive, paired neuromas (Probst's bundles) adjacent to the longitudinal cerebral fissure.

Further, the inventors have shown that in early postnatal lesion-induced acallosal animals, that an untreated, properly shaped nitrocellulose (Millipore) filter, placed adjacent to the neuromas and spanning the lesioned cerebral midline, could support the migration of immature glia (Silver, et al., *Postnatally Induced Formation of the Corpus Callosum in Acallosal Mice on Glia-Coated Cellulose Bridges*, Science, 220: 1067–1069, 1983). The glia attached to the surface of the filter to produce a cellular scaffold, which in turn provided a terrain suitable for the ectopic axons in the neuromas to traverse the midline to reform the corpus callosum.

However, the inventors only recently determined that a "critical period" existed for the formation of induced callosal axon growth to occur. The inventors noted that the stellate-shaped, GFAP-positive "activated" immature astrocytes migrated and attached to the implant by inserting a foot of their cytoplasmic processes into the pores of the filter implant. This form of gliotic response only occurred in animals younger than the eighth postnataly day (P8) and established an axon growth promoting substratum within 24–48 hours after implantation. Hence, an additional embodiment of the present invention is directed to the use of only "activated" immature (i.e. postnatal day 8 or less) astrocytes for promoting axonal regeneration.

Similarly, a further embodiment of the present invention concerns the use of "activated" immature astrocytes in injectable form or on nitrocellulose implants to promote directed axon regeneration and reduce glial scar formation in damaged spinal axons of the central nervous system. The inventors and others have demonstrated after repeatedly crushing or cutting the dorsal roots near their entrance point in the spinal cord, that the peripheral sensory fibers are regenerated only as far as the dorsal root entry zone (DREZ) of the spinal cord but no further. The problem at the DREZ is analogous to the failure of axon regeneration throughout the remainder of the CNS. Although the distance needed to reconnect the regenerating sensory fibers with their denervated dendrites in the dorsal horn of the spinal cord is relatively short (i.e. only fractions of a millimeter in the adult rat), this scant distance is normally never breached by regenerating sensory fibers in adult animals.

In order to span the gap between the sensory fibers and the denervated dendrites in the dorsal horn of the spinal cord, the inventors have developed a process for bridging the root-cord interface with a newly designed "pennant-shaped" nitrocellulose polymer (8 um pore size) implant coated with activated immature astrocytes. The results of the process indicate that the combination of the activated immature astrocytes plus the specially designed polymer implant represses scar formation locally in the cord dorsal root entry zone and stimulates axons and blood vessels to enter the CNS along the bridge surface. In addition, animals with dorsal root lesions and inserted activated immature astrocyte coated implants, exhibited remarkable functional recovery of many basic sensory-motor behaviors. Hence, a further embodiment of the present invention is directed to the use of a specially designed nitrocellulose implant coated with activated immature astrocytes to promote directed axon regeneration and repress scar formation of damaged spinal axons of the central nervous system.

SUMMARY OF THE INVENTION

In one aspect, the present invention relates to a method for promoting directed axon regeneration, including the steps of providing activated immature astrocytes and administering an effective amount of the activated immature astrocytes to damaged axons to promote axon regeneration.

In another aspect, the present invention concerns a method for promoting axon regeneration including the steps of providing activated immature astrocytes, seeding an effective amount of the activated immature astrocytes onto an implant; and inserting the seeded implant near the ends of damaged axons to promote directed axon regeneration.

In a further aspect, the present invention is directed to a method for promoting directed axon regeneration in an animal lacking activated immature astrocytes including the steps of providing activated immature astrocytes and administering an effective amount of said activated immature astrocytes to damaged axons of an animal lacking activated immature astrocytes to promote directed axon regeneration.

In still another aspect, the present invention relates to a method for promoting directed axon regeneration in an animal lacking activated immature astrocytes including the steps of providing activated immature astrocytes, seeding an effective amount of said activated immature astrocytes on to an implant, and inserting the seeded implant into damaged axons of an animal lacking activated immature astrocytes to promote directed axon regeneration.

In a still further aspect, the present invention concerns a method for promoting directed axon regeneration in an animal lacking activated immature astrocytes including the steps of inserting an implant into the central nervous system of an animal possessing activated immature astrocytes, waiting a sufficient period of time to permit an effective amount of said activated immature astrocytes to become attached to the surface of said implant, removing the implant and the attached activated immature astrocytes from the animal possessing activated immature astrocytes and inserting the implant and the attached activated immature astrocytes into the damaged axons of an animal lacking mature astrocytes to promote directed axon regeneration.

In an additional aspect, the present invention relates to a method for reducing glial scar formation, including the steps of providing activated immature astrocytes and administering an effective amount of the activated immature astrocytes to damaged neurons and axons to reduce glial scar formation.

In another aspect, the present invention concerns a method for reducing glial scar formation including the steps of providing activated immature astrocytes, seeding an effective amount of the activated immature astrocytes onto an implant; and inserting the seeded implant into damaged axons to reduce glial scar formation.

In a further aspect, the present invention is directed to a method for reducing glial scar formation in an animal lacking activated immature astrocytes including the steps of providing activated immature astrocytes and administering an effective amount of said activated immature astrocytes to damaged axons of an animal lacking activated immature astrocytes to reduce glial scar formation.

In still another aspect, the present invention relates to a method for reducing glial scar formation in an animal lacking activated immature astrocytes including the steps of providing activated immature astrocytes, seeding an effective amount of said activated immature astrocytes on to an implant, and inserting the seeded implant into damaged axons of an animal lacking activated immature astrocytes to reduce glial scar formation.

In a still further aspect, the present invention concerns a method for reducing glial scar formation in an animal lacking activated immature astrocytes including the steps of inserting an implant into the central nervous system of an animal possessing activated immature astrocytes; waiting a sufficient period of time to allow for an effective amount of said activated immature astrocytes to become attached to the surface of said implant, removing the implant and the attached activated immature astrocytes from the animal possessing activated immature astrocytes and inserting the implant and the attached activated immature astrocytes into the damaged axons of an animal lacking mature astrocytes to reduce glial scar formation.

In still another aspect, the present invention relates to a therapeutic composition for promoting directed axon regeneration comprising, in a pharmaceutically acceptable carrier, purified activated immature astrocytes.

In a still further aspect, the present invention concerns a therapeutic composition for promoting directed axon regeneration comprising, in a pharmaceutically acceptable carrier, purified embryonic through postnatal day 8 astrocytes.

In still another aspect, the present invention relates to a therapeutic composition for reducing glial scar formation comprising, in a pharmaceutically acceptable carrier, purified activated immature astrocytes.

In a still further aspect, the present invention concerns a therapeutic composition for reducing glial scar formation comprising, in a pharmaceutically acceptable carrier, purified embryonic through postnatal day 8 astrocytes.

DESCRIPTION OF THE DRAWINGS

The following is a brief description of the drawings which are presented for the purpose of illustrating the invention and not for the purpose of limiting same.

In FIG. 1a, a brain viewed from above shows a filter (I) that was placed horizontally acrossed the midline extending into each cortical hemisphere. Higher magnification of the surface of the filter showing many attached cells is illustrated in FIG. 1b. As shown in FIG. 1(c), the first axons (arrowheads) to extend across the filter do so nonfasciculated and along the glia that have attached to the implant. FIG. 1d shows that astrocytes respond to the presence of axons (Ax) by extending small processes (arrow) that encircle the axons. The magnification of the respective FIGURES is as follows: (a) ×20; (b) ×700; (c) ×2,000; (d) ×16,000.

FIGS. 2a-2c represent animals implanted at "critical" stages; postnatal days 2 (FIG. 2a) and 8 (FIGS. 2b, 2c), both examined 48 hours after implantation. A comparison of FIGS. 2a-2c to animals implanted at "postcritical" stages, 14 (FIG. 2d) and 21 (FIG. 2e) days after birth, both examined 7 days postoperatively, indicate that in FIGS. 2a-2c the glia are more stellate, sending many cytoplasmic processes into the pores of the filter, whereas the cells near the implant in FIG. 2d and FIG. 2e appear flat, lacking extensive infiltration of processes. Directly above the infiltrated stellate glia of "critical" period implants are numerous axons (asterisks; FIGS. 2a—2c), but such axons were not apparent in "postcritical" stage implants (FIGS. 2d-2e). The magnification of the respective FIGURES is as follows: (a) ×400; (b) ×125; (c) ×400; (d) ×400; (e) ×400.

FIGS. 3a, 3b, 3c, 3d, and 3e are micrographs of the corpus callosum of a previously acallosal animal implanted with a Millipore implant on postnatal day 5. When the animal was killed five weeks later, a new callosum (CC) had formed above the implant (FIGS. 3b and 3c). Further rostrally the bridge did not span the midline and was embedded in only one of the neuromas (FIG. 3a). In this region small groups of axons left the neuroma but grew ectopically along the subependymal zone within the dorsal septum (*). Uniquely, the animal had both large longitudinal neuromas (LB) and a well-developed callosum in the same plane of section as well as the ectopic ipsilateral septal projection (FIGS. 3b and 3c). This uniqueness provides a marker that insures that the animal was acallosal at the time of implantation. Horseradish peroxidase injected into the cortex of one hemisphere in the region of the de-novo-formed callosum (arrow) labels neurons on the opposite side of the brain (bracketed area of FIG. 3c; higher magnification, FIGS. 3d and 3e). The reformed callosum has grown to its appropriate region of synaptic termination (small arrows). The magnification of the respective FIGS. is as follows: (a) ×100; (b) ×100; (c) ×100; (d) ×250; (e) ×400.

In FIG. 4a, twenty-four hours after implantation numerous glia (arrowheads), some which are phagocytic (insert), have migrated out of the hemisphere and along the implant. As they attach to the implant (I) they extend cytoplasmic processes into the pores of the filter (small arrows in FIGS. 4b and 4c); note that the leading glial cell (far right) has extended few processes. In FIG. 4b, within 48 hours, glia coat the majority of the filter surface, providing a substrate on which axons (Ax) and blood vessels have extended. As shown in FIG. 4c, in some specimens 72 hours after implantation the axons fasciculate over the glia above the filter, a configuration similar to that of the normal developing corpus callosum and "sling". Note in FIG. 4c however, the absence of a glial limiting membrane. The magnification of the respective FIGS. is as follows: (a) ×500; (b) ×400; (c) ×500; insert ×4,400.

In FIG. 5a, acallosal neonates (P2) implanted with filters and examined after five days show extensive astrocytic processes within the implant (I) and within the cortex (Cx), retaining their stellate morphology. In FIG. 5b, the astrocytes in acallosal animals implanted at postcritical stages (P21) and examined after one week appear flat *within* the scar above the implant (I). The magnification of the respective FIGURES is as follows: (a) ×300; (b) ×300.

FIGS. 6a, 6b, 6c, 6d, 6e, and 6f are micrographs of coronal sections showing the staining pattern produced by antibodies against laminin protein. As shown in FIG. 6a, in critically implanted before P8 animals laminin not only appears to be confined to the basal lamina of blood vessels and the pia, but it is also along glial processes (arrows) within the filter (FIGS. 6a and 6b). When animals were implanted at postcritical stage (P21) antilaminin stained the basal lamina in the scar that extends around the implant (I) and appears continuous with the longitudinal fissure (LF; FIGS. 6a and 6d). The cells producing the laminin are flat. Post-critical period animals P34 (FIGS. 6e, 6f) implanted with glial-coated filters from P2 neonates show no scar formation and thus, a laminin staining pattern identical to critical period animals given naked implants alone (compare FIGS. 6a and 6b to FIGS. 6e and 6f). The magnification of the respective FIGURES is as follows: (a) ×100; (b) ×250; (c) ×100; (d) ×250; (e) ×100; (f) ×250.

In FIG. 7a, glia attached to the implant have a stellate morphology; microglia (M) are also apparent. Among and above the glia that have sent processes into the filter (arrows) are axons (Ax) and blood vessels (BV). As noted in FIG. 7b, the axons (small arrows) that extend into areas where basal lamina (BL arrowheads) appear positioned immediately adjacent to the glia but not to the basal lamina. Higher magnification in FIGS. 7c and 7d shows axons associated with astrocyte processes (G) containing intermediate filaments and glycogen granules. The magnification of the respective FIGURE is as follows: (a) ×4,500; (b) ×5,000; (c) ×12,000, and (d) ×12,000.

In FIG. 8a, the glia above the crushed portion of the filter (C) are flat and have a smooth surface (FIGS. 8a and 8b), whereas the glia attached to the noncrushed area (NC) are more stellate in shape (FIGS. 8a, 8b, and 8f). In places, some of the flat glia over the crushed implant, rippled and extended many very short processes (FIG. 8d). In areas where this occurred, other glia moved onto the flattened cells establishing a cellular pile (FIG. 8e). The magnification of the respective FIGURE is as follows: (a) ×200; (b) ×1,800; (c) ×600; (d) ×3,500; (e) ×1900; (f) ×2,100.

In FIG. 9a, a majority of the glia attached to the filters labeled with silver grains over the nuclei. Cells further removed from the implant surface and along blood vessels are also labeled by $^3$H-thymidine (arrows). Transplanted neonatal glia on Millipore (I) placed into post-critical-period animals (P34) retain their stellate morphology, as shown when stained with antibodies against GFAP (see FIG. 9b). The magnification of the respective FIGURE is as follows: (a) ×450; (b) ×300.

FIGs. 12a, 12b, 12c, and 12d are transmission electron micrographs at the midline of a postnatal day 17 acallosal mouse that received a pre-glial coated implant (I) from a 2-day neonate donor and was then examined six days after it resided in the host. As shown in FIG. 12a, the glia attached to the implant have retained their stellate morphology and infiltrated cytoplasmic processes. Scarring and ectopic basal lamina are absent. Among the glia are many de-novo-formed axon bundles (arrowheads). Higher magnification shows loosely fasciculated unmyelinated axons (FIG. 12b) and others (arrow) adjacent to a astrocytic processes. Two daughters cells (D) above the implant share a midbody (open arrow in FIG. 12d). Thus, transplanted cells can divide. The magnification of the respective FIGURES is as follows: (a) ×10,000; (b) ×20,000; (c) ×10,000; (d) ×3,300.

FIGS. 13a, 13b, 13c, 13d, 13e, and 13f are micrographs of GFAP immunofluorescence. These micrographs show that both immature (FIG. 13a) and mature (FIG. 13b) astrocyte coated implants (I) have GFAP positive astrocytes attached to their surface. Astrocytes were purified and allowed to age in vitro. Photomicrographs of laminin immunoreactivity in P60 acallosal mice transplanted with either immature (FIG. 13c) or mature (FIG. 13d) astrocyte coated implants. Note the lack of basal lamina staining (i.e. scarring) in the host brain receiving immature astroycytes (bracket in FIG. 13c). However, basal lamina is quite apparent in host brains receiving mature astrocyte coated implants (bracket in FIG. 13d). Basal lamina staining on the bottom of all transplants is caused by the lack of transplanted astrocytes in that portion since they were seeded on the top of the filters in culture. Autoradiograph of astrocytes transplanted into P60 mice which were labeled with $^3$H-thymidine in culture. Labeled immature astrocytes (arrows) have the ability to migrate away from the surface of the implant (FIG. 13e). Labeled mature astrocytes (arrowheads) did not appear to migrate away from the surface in the implant (FIG. 13f). The magnification of the respective FIGS. is as follows: (a) ×400; (b) ×400; (c) ×300; (d) ×300; (e) ×400; (f) ×400.

In FIG. 17a, the axons (Ax) traverse the surface of the implant along the stellate "activated" glia (i.e. inserted) that extend processes into the non-crushed portion of the filter (NC), but they turn abruptly at the crush (C)/non-crush (NC) interface. The astrocytes attached to the surface of the crushed portion were non-activated flattened (arrowheads and upper insert), displayed a mound where the nuclei reside and had lamellipodia (L in second insert) at their periphery. As noted in FIG. 17b, the axon bundle (Ax) turns perpendicularly and travels along the crush/non-crush interface. In FIG. 17c, fibers crossed over the crushed portion of the implant above a mat of glia with a flat-celled bottom layer (open arrow). The fibers then grew rostrally on another inserted group of cells on the other side of the crush (Ax at the right in FIG. 17b). Some axons were also present within the filter on the inserted activated astroglial processes. The magnification of the respective FIGURES is as follows: (a) ×400; (inserts) ×625; (b) ×3,300; (c) ×400.

FIG. 18a is a frontal view of the "pennant-shaped" nitrocellulose implant (10) containing the activated immature astrocytes (12). FIG. 18b is a cross sectional view of the "pennant-shaped" implant (10) coated with the activated immature astrocytes (12) inserted into the dorsal root cord interface. The pole portion (14) of the pennant protrudes outside the spinal cord (18) into the dorsal root (20) itself, while the broad portion (16) of the pennant-shaped implant lays in the cord (18) proper. FIG. 18c is an overhead view of the "pennant-shaped" implant (10) coated with the activated immature astrocytes inserted into the dorsal root (20) cord (18) interface.

FIGS. 19a through 19c indicate that the combination of embryonic astrocytes plus the oriented nitrocellulose implant, represses scar formation locally in the L5 dorsal root entry zone (FIG. 19b) and stimulates axons and blood vessels to enter the central nervous system along the implant surface (FIGS. 19a and 19c). FIG. 19d demonstrates the normal scar formation which occurs at the dorsal root entry zone of a root-lesioned rat. As indicated in FIG. 19d, when no nitrocellulose implant coated with activated immature astrocytes was inserted in the dorsal root-cord interface, no axonal regeneration is observed. The magnification of the respective FIGURE is as follows: (a) ×400; (b) ×25; (c) ×60; (d) ×400.

DETAILED DESCRIPTION OF THE INVENTION

Figure 1A:
FIGS. 1a, 1b, 1c, and 1d are scanning electron micrographs of acallosal mice implanted on postnatal day 2 and examined 24 hours later.
Figure 1B:
Figure 1C:

The present invention is directed to "activated" immature astrocytes (postnatal day 8 or less) and the method of utilizing the activated immature astrocytes to treat disorders of the nervous system resulting from accidents or disease which have in some way damaged the nerve tissue. According to the present invention, it has now been determined that contrary to normal adult astrocytes which promote glial scar formation, certain "critical period" activated immature astrocytes (postnatal day 8 or less) reduce glial scar formation, inhibit extensive bleeding and secondary necrosis, and promote axonal regeneration. Thus, the present invention is directed to a process for isolating, harvesting, purifying and immortalizing the "critical period" activated immature astrocytes and transplanting the activated immature astrocytes into the central nervous system of postcritical period animals in order to promote axonal regeneration and blood vessel growth and/or reduce glial scar formation and necrosis.

More particularly, in vivo testing indicates the existence of a critical period for substrate-supported axon regeneration. De-novo growth of commissural axons across the cerebral midline was observed in acallosal animals implanted with untreated nitrocellulose filter paper (pore size 0.45 mm) on or prior to day 8, but not later. During this critical period, the astrocyte glia migrated onto the implant within 12-24 hours. The activated, immature astrocytes were stellate-shaped, GFAP-positive, and have the capacity to support the growth of axons, as well as vascular elements.

In contrast, the reactive glial response in animals implanted day 14 or later after birth showed distinct differences from gliosis observed in neonates. The length of time it takes the glial cells to reach the surface of the implant (5-7 days), the extent of secondary necrosis, the degree of basal lamina production and fibroblast contamination, and the density of tissue at and around the implant all increased with age. The morphology of cells surrounding the implant also became altered and, more importantly, the 14 day old or older astrocytes lost their ability to stimulate axon outgrowth.

As a result of the above discovery, the activated immature astrocytes (postnatal day 8 or less) were harvested and transplanted into postcritical period animals (postnatal day 14 or more) in order to determine whether an environment conducive for axon regeneration could be re-established in the postcritical animals. The results (discussed in more detail below) indicate that the immature astrocytes survive implantation and reduce the deleterious sequalae of lesions in the brain. In addition, axonal regeneration and/or blood vessel growth is also enhanced. The beneficial effects observed include the reduction of necrosis and glial scar formation at the lesion site as well as stimulating and serving as a substratum for the regeneration of postcritical period callosal axons that were not otherwise observed to regenerate. Although the initial studies were performed with activated immature astrocytes (postnatal day 8 or less) harvested on millipore filters placed in the forebrain of postcritical period mice, recent studies also indicate that the same beneficial effects are observed when the activated immature astrocytes are implanted on polymers in the spinal cord region of paralyzed animals.

In addition, the activated immature astrocytes have been isolated, harvested, and purified in vitro for use in-vivo as well as in-vitro. In addition, because normal immature astrocytes mature in culture, purified activated immature astrocytes have been genetically engineered to be immortal and forever immature for in-vivo therapeutic use. Similarly, the activated immature astrocytes have been used in-vitro to promote axon growth in biological cultures.

The following examples further describe the specific practice of the instant invention:

EXAMPLE 1

A. Transplantation of Implants and Cellular Coatings

1. Insertion of the Implants

Timed pregnant C57 BL/6J mice were obtained from the Jackson Labs, Bar Harbor, Maine. The glial "sling", which forms the transient axon guidance pathway between the right and left cortical hemispheres of the brain, of 16 day embryos (E16) of timed pregnant mice (Silver, et al., supra 1982) was lesioned by inserting a microneedle into the embryos' calvarium approximately 1 mm rostral to the cranial landmark "lambda" to a depth of about 2 mm. As a result of the above process, the lesioned mice were consistently acallosal. In an experiment to test the efficiency of the technique, 50 animals were acallosal out of the 50 lesioned.

The lesioned embryos, once born, were then anesthetized and implanted with a specially designed piece of nitrocellulose filter (a 1-mm$^2$, "home-plate" shaped piece of cellulose membrane filter (Millipore), 0.45-um pore size) on postnatal day (P) 2, 5, 8, 14, and 21 and at 8 months. In the neonates the skull was still pliable and did not require drilling. An incision through the skin and cranium was made horizontally between the eyes and the skin was retracted. The surface of the skull was scraped free of tissue in order to minimize contamination of other cell types onto the implant as it was inserted. The specially designed implant was then inserted, pointed side first, 2-5 mm into the stab wound. The animals were then maintained in a normal growth environment for 2 or more days.

In addition, in order to determine whether a change in "activated" astrocyte morphology from stellate (i.e. inserted) to flat altered the efficiency of the astrocytes to provide a conducive substratum for axon elongation a second set of experiments were conducted wherein portions of the implants were precrushed midsagitally to reduce pore size before insertion into the neonatal brain according to the above process.

2. Removal of the Implants Plus Their Cellular Coatings

The implants, plus their cellular coatings, were removed from the decapitated acallosal mice 48 hours after implantation on postnatal day 2 (P2) The tissue around the implant was carefully dissected and the implant was removed with forceps which prevent the cells on the surface from being crushed or stripped away. The implants, and their cellular coatings, were then dipped in N-2 medium (Bottenstein, J. E. and G. H. Sato, *Growth of a rat neuroblastoma cell line in serum-free supplemented medium.* Proc. Natl. Acad. Sci. 79: 514-517, 1983) and placed in a humid chamber at 37° C. until they were transplanted a few minutes later.

3. Transplantation of the Implants and Their Cellular Coatings to Older Postcritical Period Hosts Host C57 BL/6J mice (at postnatal day 17, 34 or 8 months) obtained from the Jackson Labs, Bar Harbor, Maine, were made acallosal in the embryo or on the day of birth. The transplants (i.e. the implants plus their cellular coatings) were inserted in the same manner as described above.

The animals were then killed 0.5, 1, 2, 3, 5, 6, and 7 days and 2 months after implantation by perfusion through the heart. The perfusion was performed in two steps: first, 2-5 ml of an 0.15M phosphate buffer solution at 37° C. was injected into the left ventricle, followed by fixative (0.5% glutaraldehyde/2.0% formaldehyde in the same buffer, with 0.5% DMSO). The brains were quickly dissected from the cranium and placed in the same fixative overnight at 4° C. The filter and surrounding tissue were subsequently embedded in Spurr's plastic using standard procedures. Serial 1-um sections were taken through the implant and stained with toluidine blue. Certain regions were sectioned ultra-thin, stained with uranyl acetate and lead citrate, and viewed with a Zeiss 109 electron microscope. For specimens examined by a scanning electron microscope (SEM), the tissue above the implant was gently dissected away and the specimens were osmicated and dehydrated through a graded series of alcohols. The samples were critical-point dried in a Balzers CPD 020 and sputtercoated with gold with an Edwards E306 device. After being mounted on aluminum stubs, they were viewed with an Etech scanning electron microscope.

B. Immunohistochemistry

Variously aged postnatal C57 BL/6J mice made surgically acallosal and containing implants for one week were anesthetized and perfused through the heart with 2-5 ml of 4.0% formaldehyde in phosphate buffered saline (PBS, pH 7.5). The brains were dissected from their calvaria and immersed in fixative for 2 hours, then cryoprotected by using a graded series of sucrose PBS solutions (10% sucrose, PBS solution for 30 minutes, 15% for 30 minutes and 20% for 2 hours to overnight); 10-um sections were taken on a Slee HR Mark II cryostat microtome.

Polyclonal antibodies against purified laminin and fibronectin were received from Dr. G. Martin (NIH). The sera were used at dilutions of 1:50. Antibodies against glial fibrillary acidic protein (GFAP) were provided by Dr. Robert Miller (Case Western Reserve, Cleveland, Ohio). They were diluted 1:1,000 and applied for 1 hour at room temperature. Sections were rinsed in PBS (3-15 minutes washes) and incubated with peroxidase-conjugated goat antirabbit IgG (Cooper Biomedical, Malvern, PA) at a dilution of 1:100 for 30 minutes at room temperature or goat antirabbit FITC at a dilution of 1:50 for 1 hour. Sections were rinsed again in PBS, and peroxidase conjugates were incubated in a solution containing 15 mg DAB (3,3 diaminobenzidine tetrahydrochloride; Eastman Kodak Co., Rochester, NY) per 100 ml Tris (pH 7.5) for 30-45 minutes at room temperature in the dark.

C. Horseradish Peroxidase Injections

In order to determine the location of cell bodies that contribute axons to the implant surface, acallosal mice implanted on postnatal day 5 (P5) and allowed to survive 5 weeks were given a single, small wedge of crystalline horseradish peroxidase (Sigma VI) that was inserted (with a spinal needle) very superficially into the cortex of one hemisphere of the brain in a region immediately lateral to the implant. On the following day the animals were killed and perfused with 0.5% glutaraldehyde and 2% formaldehyde in 0.15M PBS. Brains were removed and placed in the same fixative for 4 hours. Sections were cut on a vibratome at 65 um and incubated in 50 mg of DAB in 100 ml Tris buffer (pH 7.5) for 20 minutes. A solution of 0.6% hydrogen peroxide was added and the sections were incubated 15-20 minutes longer. Sections were counterstained with neutral red and mounted on the slides.

D. $^3$H-thymidine Autoradiography of Transplants

Acallosal neonates, implanted with filters on postnatal day 2 (P2), were injected intraperitoneally with $^3$H-thymidine (5 uCi/g of body weight) at 6, 18, and 30 hours after implantation. Implants were removed 18 hours after the last injection and transplanted into postnatal day 23 (P23) surgically induced acallosal mice obtained from Jackson Labs. The mice were perfused 4 days after transplantation and prepared for plastic embedding. Sections 1 um thick were mounted on slides and coated with Kodak NTB-2 autoradiographic emulsion. The coated slides were placed in light-proof containers and stored at $-5°$ C. for 6 weeks. Slides were processed for photography at 18° C.

RESULTS

A. Determination of the "Critical Period" in Astrocytes for Axon Elongation

Figure 1D:
Figure 4A:
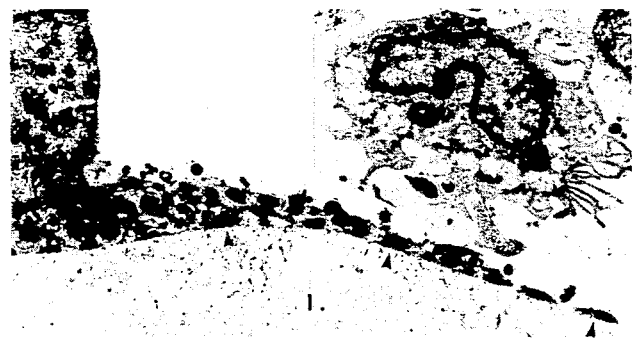
FIGS. 4a, 4b, and 4c are micrographs of coronal sections through filters implanted into postnatal day 2 acallosal mice and examined 24 (FIG. 4a), 48 (FIG. 4b), and 72 (FIG. 4c) hours later.
Figure 4B:
Figure 4C:
Figure 16:
FIGS. 16a and 16b are scanning electron micrographs of axons extending over the glia (asterisk) attached to a filter implanted into an acallosal postnatal (day 2) and examined 48 hours later. The low power insert (FIG. 16a) shows callosal axons extending from only one hemisphere, out of the neuroma (LB) and across the implant (I). The caudal tip (CT) and borders of the filter are apparent. Higher magnification (FIG. 16b) shows large fascicles of axons traversing the implant towards the opposite hemisphere. However, not all axons retain their orientation and some wander in the middle of the filter (arrows). The magnification of the respective FIGURES is as follows: (a) ×80; (b) ×700.

An analysis of the scanning electron micrographs of the acallosal mice implanted with untreated nitrocellulose bridges at various stages (P2, 5, 8, 14, and 21 and 8 months) indicated that the glial response at 24-48 hours after implantation produced a terrain along the filter that was suitable for axon extension only in animals that were implanted before or on postnatal day 8 (P8). This was shown by the presence of many unmyelinated axons interspersed among the attached glial cells (astrocytes). See FIGS. 1 and 16. The micrographs indicated that glia in the P2 and P8 implants coated the majority of the implant surface, providing a substrate on to which axons and blood vessels were extended (FIGS. 4a through 4c). In P2 and P8 implants, the glia (astrocytes) on the filter appeared to be stellate in shape and respond to the presence of axons by sending out many cytoplasmic extensions around the fibers. See FIG. 1d.

However, the CNS glial response generated by implantation of animals on or later than postnatal day 14 (P14) did not produce a terrain readily suitable for axon extension. The glial in the P14 animals appeared to be flat and lacked extensive infiltration of processes. The 27 animals given naked, untreated implants postnatally at 2 and 3 weeks and 8 months showed little or no growth of axons on to the implant when examined at 1 week and as late as 2 months after implantation. See FIG. 2.

Figure 3B:

B. Determination of the Location of the Cell Bodies that Contributed Axons to the Implant Surface A review of the micrographs concerning the horseradish peroxidase injections, indicated that the representative sections contained retrogradely labeled cortical neurons in a position contralateral and homotopic to that of the injection site (See FIG. 3). Thus, the results demonstrated that some of the commissured axons emerged from one region of the brain and grew across the midline to the opposite region of the brain, using the implant as a pathway.

C. Host Glial Response to Nitrocellulose Bridges Implanted at Various Postnatal Ages Implantation of acallosal mice at various stages was done not only to evaluate the ability of the glial coating to provide an adequate substratum for axonal elongation but also to compare age-related changes in the host gliotic response. The micrographs showed that when implants were placed within the presumptive callosal pathway of acallosal mice at P2 and P8, the glial cells rapidly migrated onto the surface of the filter during the first 12-24 hours after implantation (See FIG. 4). The glial cells attached themselves to the implant by extending their cytoplasmic processes deep into the implant's 0.45 um pores.

The identification of the glial elements on the filter as astrocytes, as well as the extensive branching of their processes into both the prosthesis and encompassing tissue, were dramatically shown in the GFAP-stained sections. See FIG. 5. In P2 implants there were only a few macrophages around the filter 48 hours after implantation and there was no evidence of tissue necrosis or persistant bleeding (See FIG. 4).

In addition, the GFAP results demonstrated that the rapidity of astrocyte movement onto the filter and attachment with the filter decreased gradually as the age of implantation increased. In P8 implants examined after 48 hours, many GFAP-positive glia were already attached.

In contrast to P2 and P8 neonates, animals implanted on P14 and P21 showed only slight glial activity after implantation. Filters examined at this stage were coated mainly with degenerating tissue and vascular elements. Thus, the reaction and migration of glia onto the filter in animals implanted on or later than P14 required a longer period of time, often taking a full week for cells to reach the vicinity of the filter.

Figure 2A:
FIGS. 2a, 2b, 2c, 2d, and 2e are micrographs of coronal sections through the nitrocellulose bridge (I) and associated tissue of the hemispheric midline of acallosal mice.
Figure 2B:
Figure 2C:
Figure 2D:
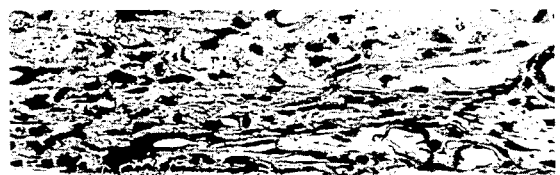
Figure 2E:
Figure 5A:
FIGS. 5a and 5b are micrographs of coronal sections illustrating the staining pattern for antibodies against GFAP in animals implanted at critical and postcritical ages.
Figure 5B:
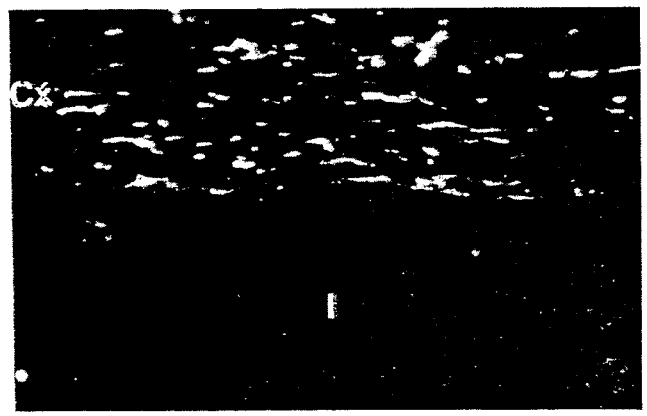

Moreover, the reactive older astrocytes had a conspicuous change in shape from stellate (i.e. inserted) to flat (compare FIG. 2a with FIG. 2e; also FIG. 5a with FIG. 5b). Macrophages with inclusions, mesenchymal tissues, and large amounts of necrotic debris always persisted within these developing scars. Another significant variation of the host glial reaction in older animals was the relative inability of the mature form of reactive astrocyte to insert processes into the implant. Filters introduced intracerebrally at later stages (P21 and 8 months), and examined after 7 days, had limited penetration of glial processes into their pores (FIG. 2). Rather than inserting, the glia flattened on the surface of the filter and encapsulated the prosthesis by forming sheets several cell layers thick.

The anti-GFAP staining pattern at P21 showed sheets of flattened astrocytes having only a few short processes penetrating into the implant (FIG. 5). These flattened astrocytes were often surrounded by nonstaining arachnoidal cells that composed a much larger proportion of the cell population encompassing the implant than at earlier stages.

Figure 7A:
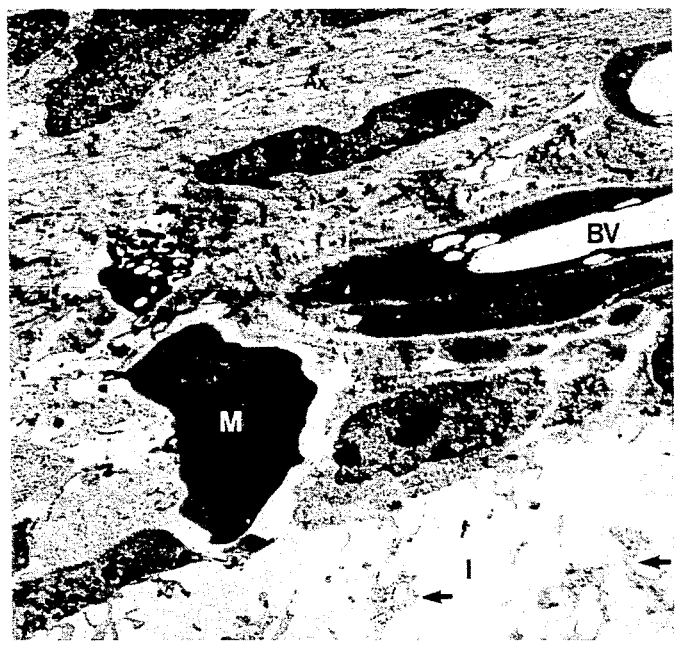
FIGS. 7a, 7b, 7c, and 7d are transmission electron micrographs of acallosal mice implanted 8 days after birth and killed 48 hours later.
Figure 7C:
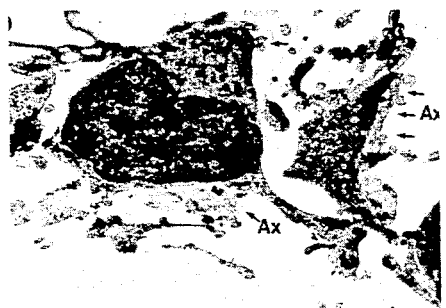
Figure 7C:
Figure 7B:
Figure 7D:
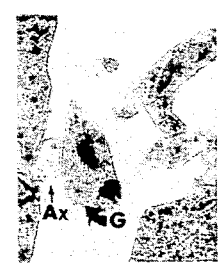
Figure 8A:
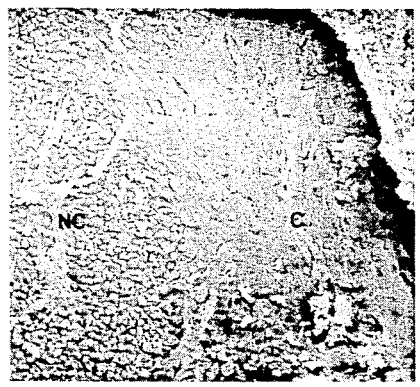
FIGS. 8a, 8b, 8c, 8d, 8e, and 8f are scanning electron micrographs of acallosal mice implanted on postnatal 2 with partially crushed filters and examined 48 hours later.
Figure 8B:
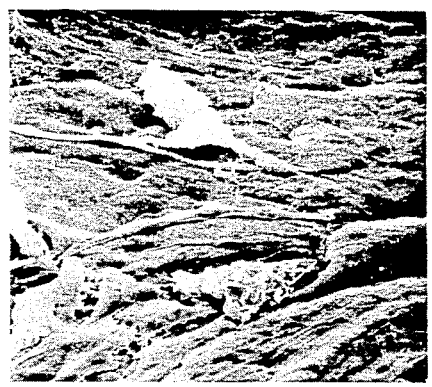
Figure 8C:
Figure 8D:
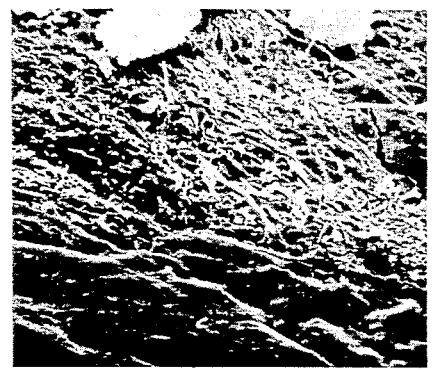
Figure 8E:
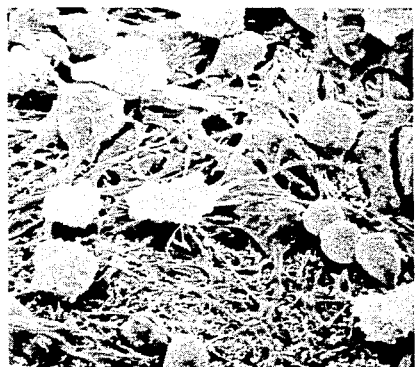
Figure 8F:
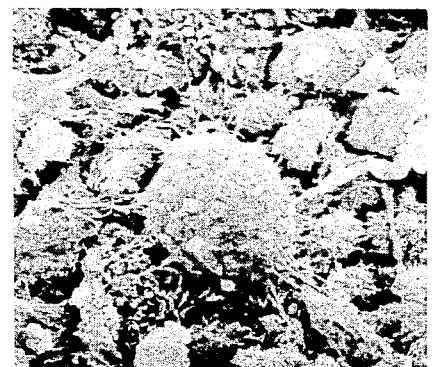

D. Extracellular Matrices Associated With Gliotic Response at Different Ages The gliotic reaction that appeared 2-7 days after implantation in P2 neonates did not stimulate the production of collagen fibers or basal laminae within the parenchyma of the CNS. Only basal laminae that normally occur around capillaries and at the pial surface could be found. However, when animals implanted at P2 were examined for laminin (a major protein component of basal lamina), an unusual staining pattern was revealed. As expected, laminin appeared to be concentrated in the basal laminae of the blood vessels and the pia mater throughout the brain. However, laminin was also found within the pores of the filter in regions containing inserted glial processes, sites having no observable amounts of basal lamina (compare FIGS. 6a, 6b with 6c, 6d), as well in collagen associated with glial scar. Ectopic basal laminae first appeared in small, isolated patches among cells surrounding the implant in some P8 individuals examined after 2-7 days. Interestingly, in P8 animals, axons were not observed juxtaposed to the ectopic basal lamina. However, axons were observed clustered along the plasma membrane of astrocytes less than 10 um away from the basal lamina (FIGS. 7b-d). The antilaminin staining within the pores of the filter was greatly reduced or absent in brains implanted on or later than P14 (FIG. 6d). Collagen fibers were seen throughout the scar, occupying spaces between cells and cell layers. Transmission electron microscope (TEM) examination of the banding pattern for the fibers identified them as being composed of type I collagen.

E. Axon Reaction to Flattened Astrocytes in Postnatal Day 2 Neonates Induced by Compressing the Pores of the Implant Observation of the scanning electron micrographs taken 48 hours after the insertion of crushed implants on postnatal day 2, indicated that many of the GFAP-positive astrocytes in the crushed region spread out to become flat and often formed a confluent monolayer. In contrast, the astrocytes that accumulated in layers over the uncrushed region of the implant were stellate with many ruffles, blebs, and cytoplasmic extensions. (See FIG. 8).

Figure 17A:
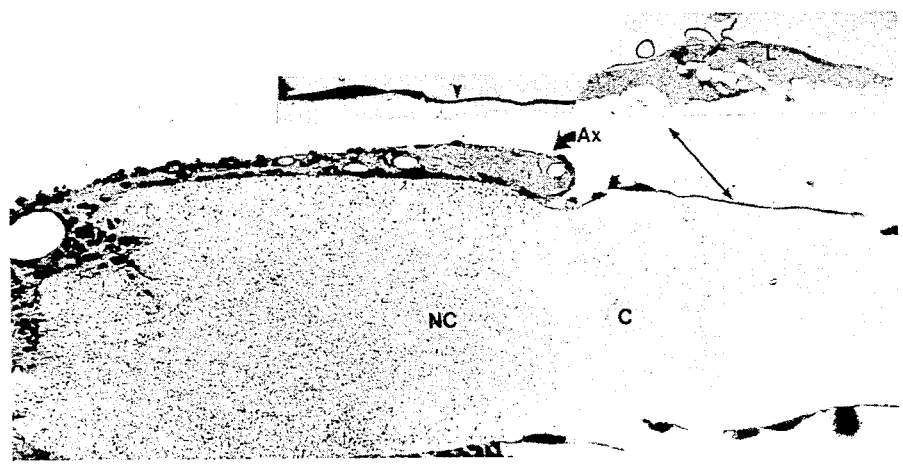
FIGS. 17a, 17b, and 17c are micrographs of coronal sections through a partially crushed filter implanted into a postnatal day 2 acallosal mouse and sacrificed 48 hours later.
Figure 17B:
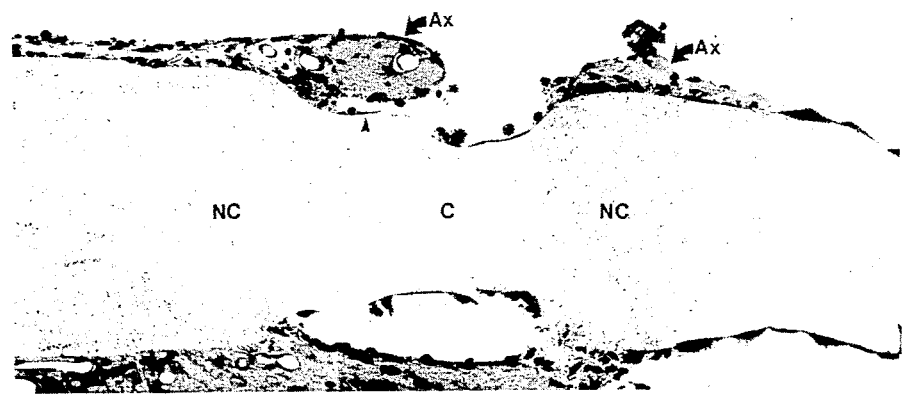
Figure 17C:
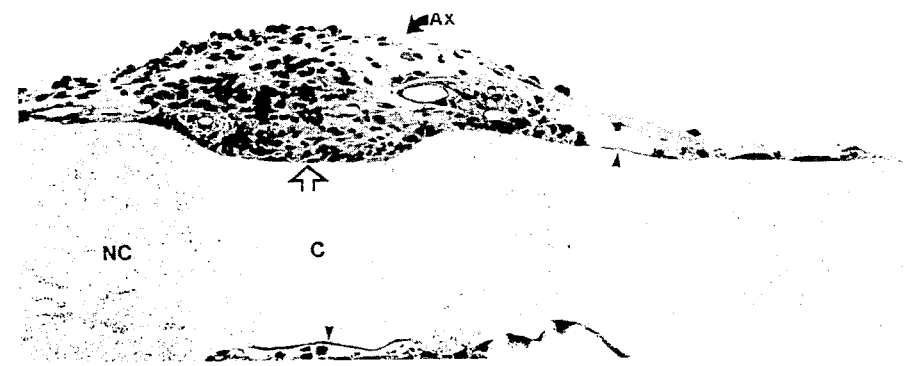

In addition, the micrographs indicated that the growing axons extended over the "activated" stellate-shaped astrocytes infiltrating the porous portion of the implant but did not grow among the flattened astrocytes on the crushed portion. (See FIG. 17) This experiment also demonstrated the importance of a proper pore size in the polymer for maintaining the astrocyte in an "activated" form when it is transplanted on nitrocellulose.

Figure 9A:
FIGS. 9a and 9b are micrographs of coronal sections of postnatal day 27 (P27) animals that received transplanted filters precoated with glia from neonates that were injected with $^3$H-thymidine.
Figure 9B:

F. Transplantation of Glial-Coated Implants From Neonatal to Postcritical Period Animals An analysis of coronal sections of postcritical period animals (i.e. P14 or greater) that received transplanted filters precoated with glia from neonates that were injected with $^3$H-thymidine indicated that many of the inserted glia were indeed transferred and survived transplantation. (See FIG. 9). Silver grains were observed not only above glia attached to the filter but also above those along blood vessels which were well away from the surface of the implant. Thus, transplanted glia can migrate from the filter surface onto the blood vessels and may be able to reduce bleeding.

In addition, the micrographs indicated that the brains of animals receiving the transplants displayed distinct changes in glial reaction around the transplant when compared with those of the same age receiving untreated implants. Implantation of naked filters into P14 or older animals consistently resulted in rampant tissue degeneration, followed by the formation of a dense, flat-cell form of glial scar associated with extensive basal laminae and collagen fibers. (See FIG. 10).

Figure 10A:
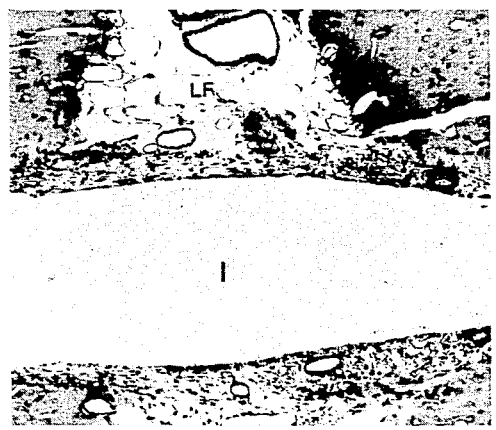
FIGS. 10a, 10b, 10c, and 10d are micrographs of coronal sections of untreated implants placed into post-critical acallosal animals (FIGS. 10a and 10b) and transplanted filters precoated with glia harvested from neonates (FIGS. 10c, and 10d). The reacting cells along the untreated filter (FIGS. 10a and 10b,) are arranged in sheets and have a flattened morphology, with few processes extending into the implant. In contrast, the gliotic reaction produced in the postcritical brain by the transplant resembles critical period implanted animals. Numerous inserted processes (arrowheads) from stellate cells and minimal scar formation or necrosis are evident (FIGS. 10c and 10d). The magnification of the respective FIGURES is as follows: (a) ×125; (b), ×400; (c) ×125; (d) ×400.
Figure 10B:
Figure 10C:
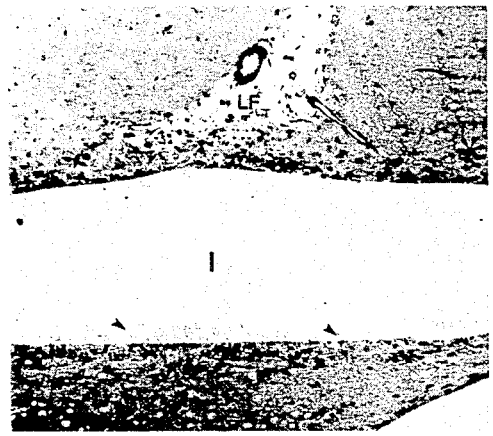
Figure 10D:
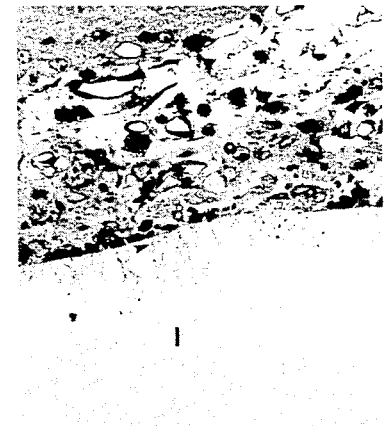
Figure 11:
FIG. 11 is a transmission electron micrograph of the host/donor interface (far lateral to the midline) from a P17 acallosal animal that was given a precoated glial implant (transplant) and examined after six days. The asytrocytes attached to the implant (I) retain their inserted processes which are rich in intermediate filaments (arrow). The cortex above the attached glia shows little tissue degeneration and no scar formation. The magnification in FIG. 11 is ×12,600.
Figure 14A:
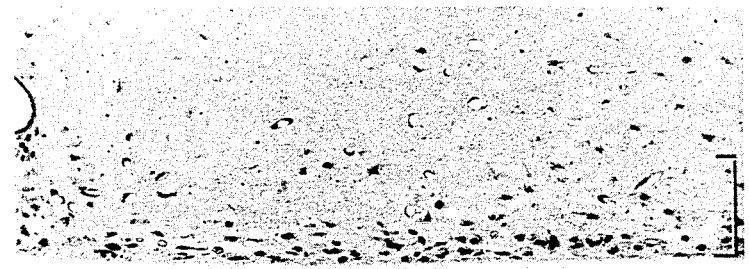
FIGS. 14a and 14b are photomicrographs of immature (FIG. 14a) and mature (FIG. 14b) astrocyte coated filters (I) which were implanted into P60 acallosal mice. Host brains of animals implanted with immature astrocytes (culture 4 days) had minimal scar formation and tissue degeneration (area in bracket in FIG. 14a). In contrast, the site of injury around implants coated with mature astrocytes (28 or more days in culture) developed a glial-mesechymal scar similar to that observed in adult mice implanted with untreated filters (area in bracket in FIG. 14b). The magnification of the respective FIGURE is as follows: (a) ×400; (b) ×400.
Figure 14B:
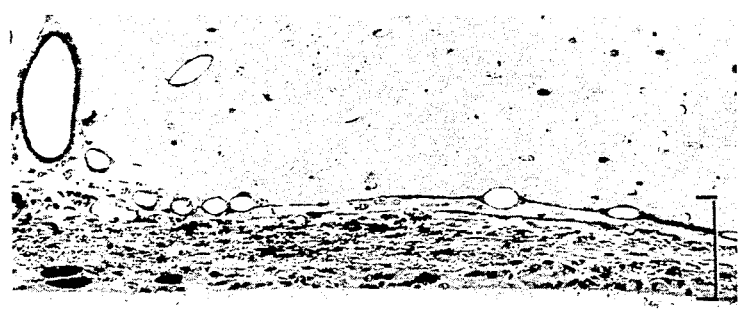
Figure 15A:
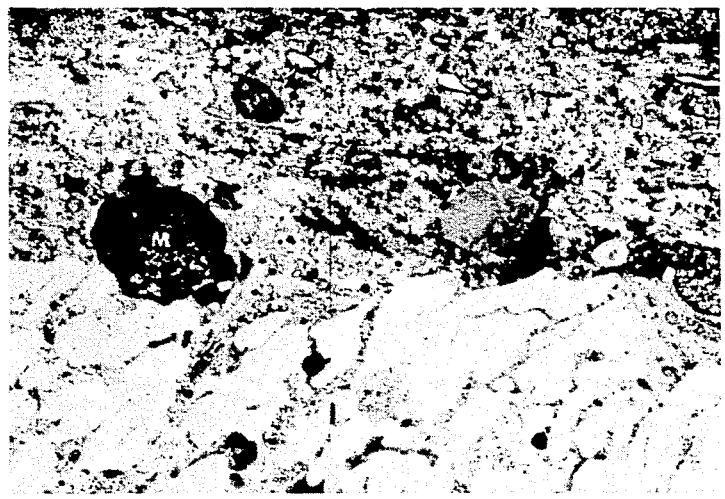
FIGS. 15a and 15b are transmission electron micrographs of the surface of an immature astrocyte coated implant (I) which was transplanted into a P60 acallosal mouse. Astrocytes containing intermediate filaments (gf) cover much of the surface of the implant (FIGS. 15a and 15b). However, there still exists a few monocytes (M) and small pockets of basal laminae (arrowheads). In the region of the cortex above the implant are intacted neutrophils containing unmyelinated and myelinated axons (arrows). Transmission electron micrograph of the scar that formed in response to the transplantation of a mature astrocyte coated implant (I) into a P60 acallosal mouse. The glial-mesenchymal scar contains collagen (cf), fibroblasts (large arrowheads) and basal laminae (small arrowheads) and fibroblasts (FIG. 15b). The magnification of the respective FIGURE is as follows: (a) ×4,400; (b) ×4,400.
Figure 15B:

In contrast, the majority of animals given transplants of activated immature glia (i.e. postnatal day 2 through 8) showed no scar formation, little basal lamina production, and negligible amounts of tissue necrosis and bleeding. In essence, the host gliotic response in transplanted animals became indistinguishable from animals implanted with naked implants during critical stages (FIGS. 10c, 10d). The transplanted animals also showed an antilaminin staining pattern identical to that seen in mice implanted on P2 (compare FIGS. 6a and 6b with FIGS. 6e and 6f). Most transplants examined 3-6 days after insertion showed (in regions where donor glia were present) little or no cellular debris and only a few macrophases at the donor/host interface (see FIGS. 10c, 10d, 11). The astrocytes along the surface of the implant formed multiple branches that interdigitated with the injured cortex, appearing to "knit" the artificial material with the tissue of the living host. In such animals (lateral to the longitudinal fissure), normal-appearing neuropil was present as close as one cell layer from the transplant (FIG. 11). In these successfully transplanted animals, there was minimal invasion of arachnoidal cells into the wound site. However, in a few instances, dense collagenous scars with layers of basal lamina, fibroblasts, and flattened glia were located in discrete regions of tissue adjacent to areas of the transplant. This occurred primarily in those regions that lacked the penetrating, stellate form of astrocyte.

G. Induced Axon Growth Over Glial Transplants

The coronal sections of a number of the postcritical period animals which had received implants with transferred glia, several hundred "regenerating" or sprouting axons were observed at the previously lesioned cerebral midline among the transplanted glia attached to the implant. (See FIG. 12). The axons were all unmyelinated and bundled in small fascicles surrounded by glia.

DISCUSSION

A summary of the results produced in the above example is set forth below in Table I.

TABLE I

Changes That Occur During and After Gliotic Reaction Induced When Acallosal Mice Are Implanted With Nitrocellulose Filters at Critical and Post Critical Stages, and When Implants Are Transplanted From Neonates to Post Critical Period Animals[1]

| | Critical[2] | | Post Critical | Transplant |
|---|---|---|---|---|
| | P2 | P8 | P14-adult[2] | P2 to P17, 34[3] |
| Number of inserted GFAP+cells | +++ | ++ | — | ++ |
| Laminin along glial processes in filter | + | + | — | + |
| Axon outgrowth over filter | +++ | ++ | — | + |
| Necrosis | — | + | +++ | + |
| Blood surrounding filter | — | + | +++ | + |
| Basal lamina | — | + | +++ | + |
| Collagen | — | + | +++ | + |
| Astrocyte shape | Stellate | | Flat | Stellate |
| Inserted glial processes | +++ | ++ | — | ++ |
| Time for glia to react to implant | 24–48 hours | | 5–7 days | |

[1]The + — system represents an overall impression of the observable preference or absence of the described reactions.
[2]Untreated implants.
[3]Implants of P2 critical period mice.

The present example demonstrates the existence of a "critical period" of less than postnatal day 8 for substrate-support axon regeneration. The de-novo growth of commissural axons across the cerebral midline was observed in acallosal animals implanted with untreated Millipore on or prior to postnatal day 8. In addition, the retrograde labeling studies using Horseradish peroxidase showed that such fibers originated from cells of the cortex and terminated in the appropriate homotopic locations in the opposite hemisphere of the brain.

Moreover, in young mice (implanted before day 8) astrocytes did not produce a scar around the filter but instead sent many processes into the pores of the filter where the immature astrocytes produced a substrate which supported blood vessels and neurite growth. However, the results indicated that astrocytes in older mice (implanted on or later than postnatal day 14) failed to incorporate the filter within the brain and, instead, produced a glial-mesencymal scar which did not support axon growth. The change in the brain's response to wounding, incorporation of implant, and support of axon growth indicated the presence of a "critical period", for substrate supported axon-elongation.

During the critical period, the migration of astrocytic glia onto the implant and the insertion of their processes are extremely rapid events occurring within 12-24 hours. The activated astrocytes are stellate-shaped and support axonal elongation. During and after the initial glia invasion phase, the population of cells that moves onto the implant has the capacity to support the growth of axons, as well as vascular elements. The majority of these cells are GFAP+astrocytes and, while in their youth, they not only have the ability to erect a three-dimensional network of proceeses separated by wide extracellular spaces, they also appear to respond to the presence of growing axons by extending additional cytoplasmic processes around the fibers.

In contrast, the results from the above example indicate that the reactive glial response in animals implanted 14 days or later after birth showed distinct differences from gliosis observed in neonates. The length of time it takes glial cells to reach the surface of the implant site, the extent of secondary necrosis, the degree of basal lamina production and fibroblast contamination, and the density of tissue at and around the implant all increase with age (see Table I). The morophology of cells surrounding the implant also becomes altered (i.e. becomes flat as opposed to stellate in shape) and, most importantly, these cells lose their ability to stimulate axon outgrowth. Thus, in contrast to adult "reactive" gliosis (i.e. greater than postnatal day 14), the gliotic response in neonatal mammals (i.e. on or prior to postnatal day 8) is an active rather than reactive phenomenon and, when controlled geometrically with a prosthesis, can be considered a beneficial and constructive process.

As a result of the above discovery, activated immature astrocytes (taken before postnatal day 8) were transplanted into older animals to determine whether their "activated" effect could be transferred into the older animals to reduce the amounts of tissue degeneration and glial scarring, as well as to determine whether the activated immature astrocytes could reestablish an environment conducive to axon regeneration. The results of the $^3$H-thymidine tests indicated that when activated astrocytes were removed from a neonate (retaining structural integrity with a polymer prosthesis) and transferred to a more mature or adult acallosal animal, that most of the activated astrocytes were transferred and survived. Similarly, the host gliotic response in the transplanted animals implanted with the activated astrocytes were indistinguishable from "critical" stage mice implanted with naked implants. Hence, the above results indicate that when activated astrocytes were implanted into an adult acallosal animal, an environment conducive for axon regeneration was reestablished in the host animal.

Moreover, the micrographs indicated that there was no evidence of tissue necrosis or persistant bleeding or scarring in the transplanted animal. The lack of extensive tissue degeneration and bleeding and scarring in the transplanted animals suggests that the transplanted astrocytes increased the survivability of cortical tissue near the site of the injury. Thus, the results demonstrate that the transplantation of "activated" astrocytes into post-critical period animals buffers the traumatic effect of the wound itself.

EXAMPLE 2

Transplantation of Purified Activated Immature Astrocytes into Post-critical Period Animals A. Preparation of Purified Activated Immature Astrocytes A highly purified population of "activated" immature astrocytes (before postnatal day 8 astrocytes) was prepared according to the following process. Cerebral cortices of four newborn C57 BL/6J mice obtained from the Jackson Labs were collected and cut into 1 mm pieces in 5 ml of calcium, magnesium-free Minimal Essential Medium (MEM-CMF). Trypsin (50% volume at 0.10%) was then added and the cells were incubated for 30 minutes at 37° C. Ethylenediamine-tetra acetic acid (EDTA) was then added (1 ml of 0.025% EDTA/5 ml of MEM-CMF) and incubated for 10 minutes. After incubation, the supernatant was then carefully removed and replaced with 2-3 ml of a mixture containing soy bean trypsin inhibitor (SBTI, 0.52 mg/ml), DNase (0.04 mg/ml) and bovine serum albumin (3 mg/ml) in Delbecos Modified Eagles Medium (DMEM). The tissue chunks were gently mixed and allowed to settle. The supernatant was removed and replaced by DMEM with 10% fetal calf serum (FCS). The tissue was triturated 5 times through a fire polished pasteur pipette. This was repeated once more with a second pipette that was fire polished a little longer so that the opening was approximately one third the diameter of the original pipette. The cell suspension was placed on ice (in a sealed 15 ml conical centrifuge tube) for 5 minutes and then centrifuged for approximately one minute at 100 rpm. The cell supernatant containing a suspension of single cells was transferred to another tube.

The cells were then counted and plated at a density of $2.0 \times 10^3$ cells/25 cm in a flask which had been previously coated with 0.1 mg/ml polylysine. The cells were pelleted by centrifugation at 1000 g and suspended in 5 ml of 50% astrocyte conditioned medium (i.e., medium that had been taken from another 4 day culture containing astrocyte only) in DMEM containing 10% FCS. The majority of the astrocytes usually attached themselves to the culture plate within six to eight hours. Within this period of time few neurons and non-astrocyte cells were attached to the dish. The non-astrocyte cells could easily be removed when the flask was shaken vigorously by hand. The cell suspension was then removed and fresh medium was added.

The cycle of shaking was repeated several times until only a few rounded cells appeared among the spreading cells. The cultures were shaken and refed once a day until all of the rounded cells were removed. This usually took three days. Hence, the resulting activated immature astrocytes obtained by this process were usually postnatal day 4 in development.

In order to obtain activated immature astrocytes which are embryonic, as opposed to postnatal in development, the above procedure was repeated utilizing embryonic day 18 (E18) fetal rat donors.

B. Preparation of Mature (P14 or older) Astrocytes

A portion of the above immature astrocytes were allowed to develop into mature astrocytes by the following procedure. Within 5-7 days after the initial plating, the astrocyte cultures became confluent. To replate the astrocytes, the media was removed, the cells were washed with MEM-CMF containing 0.02% EDTA and trypsin. This mixture was removed and only a few drops of this fresh medium was added back. The astrocytes were then incubated for 5-10 minutes until cells detached from plate, suspended in DMEM and 10% FCS and transferred to a 75 cm culture flask. Two days after replating, the cultures were treated with a 2 day pulse of cytosine arabinoside ($2.5 \times 10^{-5}$M). The addition of Ara-C after each replating left a few dead cells, but controlled the proliferation of fibroblasts. Mature astrocytes were harvested from cultures 28 days or older.

C. Seeding of the Nitrocellulose Implants

The astrocytes produced above were removed from their cultures using MEM-CMF containing 0.02% EDTA and trypsin. After approximately 10 minutes, cold DMEM with SBTI and DNase were added to the cell suspension. The cell suspension was then pelleted by centrifugation at 1000 g for five minutes. The supernatant was removed and the astrocytes were resuspended in 1 ml DMEM. The astrocytes were then pelleted and resuspended in DMEM a total of three times, the last in only 200 ml DMEM. Cell viability and number were then determined by using trypsin blue exclusion which shows that many cells survive the procedure.

Figure 18A:
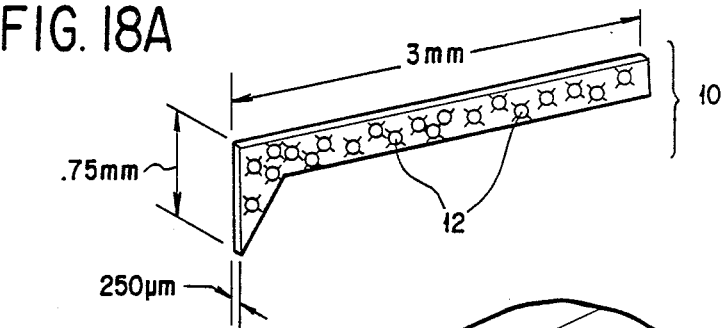
FIGS. 18a, 18b, and 18c are schematic drawings demonstrating the placement of the "pennant-shaped" nitrocellulose implant in the dorsal root entry zone of the spinal cord.
Figure 18B:
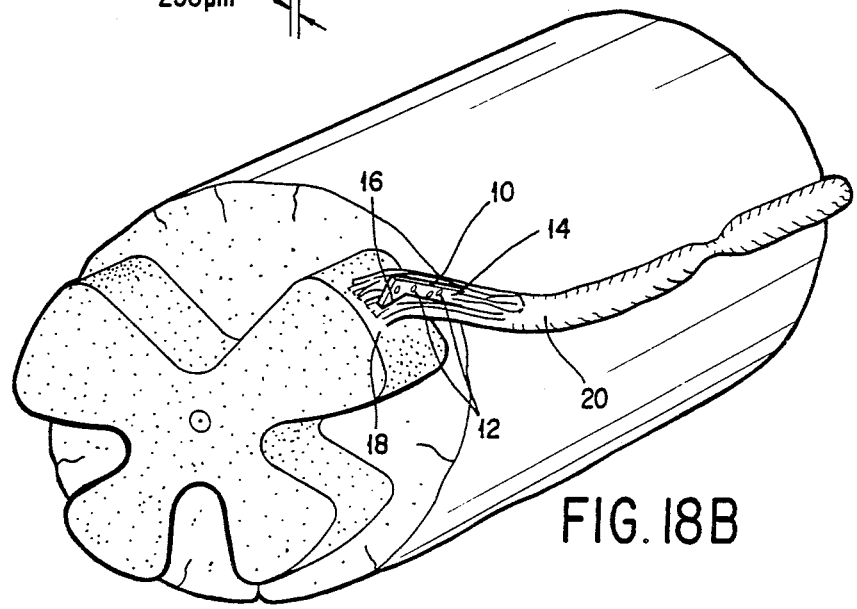
Figure 18C:
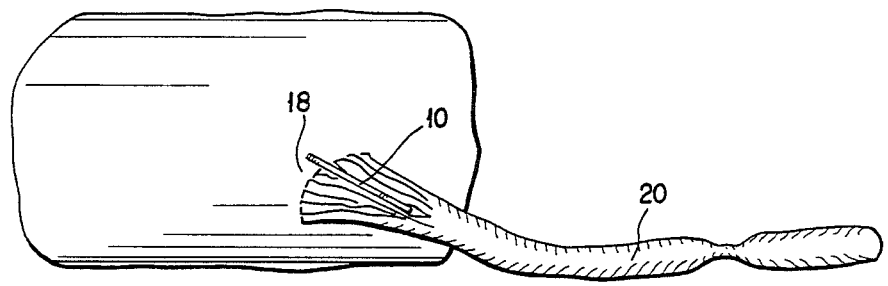

The implants to be inserted into the forebrains and spinal cords of the host animals were prepared out of various pore sizes of nitrocellulose filter paper. The implants to be inserted into the forebrain of postnatal day 60 (P60) acallosal mice were prepared out of 0.45 um pore size nitrocellulose filter paper and were of the same "home plate" shape and size as the implants defined in Example 1 (i.e. 1-mm$^2$). The implants to be inserted into the dorsal root entry zone (DREZ) of the spinal cords of the root-lesioned adult rats were prepared out of 8.0 um pore size nitrocellulose filter paper and were "pennant" shaped of a size approximately 0.75-1.0 mm$\times$3.0 mm$\times$250 um. See FIG. 18.

Approximately 10 ml of the activated immature astrocytes were then seeded on to the nitrocellulose implants at a density of $10^7$ cells/ml (about $10^5$ astrocytes/implant). The astrocyte suspension usually formed a bead on the surface of the filter, and was incubated for two hours at 37° C. A 100 ml drop of DMEM was then carefully placed over the nitrocellulose implant and the astrocytes were allowed to attach themselves to the filter by incubation over night.

The above seeding process was then repeated to produce the comparison implants containing the mature

MISSING PAGE TEMPORARY NOTICE

PATENT # 4900553 FOR ISSUE DATE 2-13-90 HAS BEEN SCANNED, BUT WITH MISSING PAGE(S). UPON RECEIVING OF MISSING PAGE(S), THE ENTIRE DOCUMENT WILL RE RESCANNED. PLEASE CALL IMAGE DATA ADMINISTRATION STAFF OF 557-6154 IF YOU HAVE A QUESTION. ASK FOR DAVE GROOMS, ANITA YOUNG OR POLA JONES.

THIS NOTICE IS FOR THE MISSING PAGE CONTAINING:

COLUMN # 21/22

N/A at Boyers
7/30/92 transplants is greatly reduced when compared to animals implanted on P14 or older. Difference between acallosal mice implanted on P21 and those implanted on P2, 8, or transplanted is significant to P less than 0.01.

Figure 19A:
FIGS. 19a, 19b, 19c, and 19d are micrographs showing the placement of the ∓pennant-shaped" nitrocellulose implant in the L5 dorsal root entry zone of the spinal cord of a 180 day or older rat.
Figure 19B:
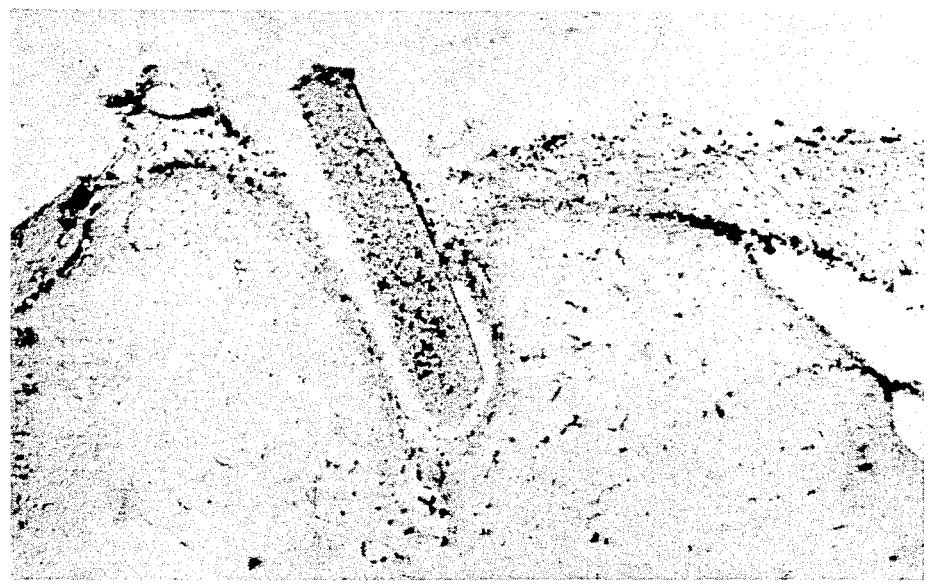
Figure 19C:
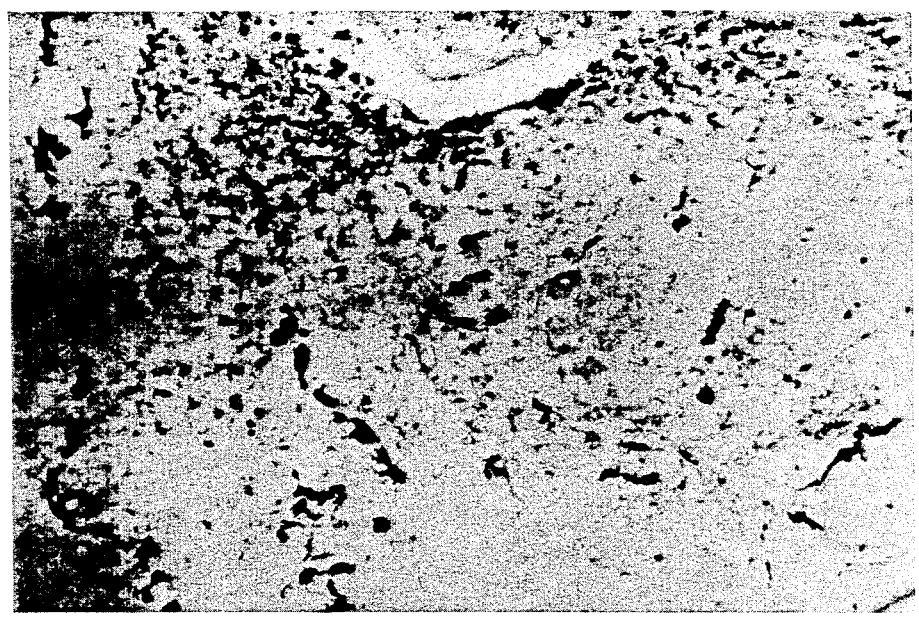
Figure 19D:

B. Transplantation of Purified Activated Immature Astrocytes into the Dorsal Root of the Spinal Cord The micrographs obtained of the pennant-shaped nitrocellulose implant coated with purified activated immature rat astrocytes inserted in the dorsal root of the spinal cord indicate that the combination of embryonic astrocytes plus an oriented nitrocellulose implant represses scar formation locally in the spinal cord dorsal root entry zone (DREZ) and stimulates axons and blood vessels to enter the central nervous system along the implant surface. (See FIGS. 19a through 19c). In addition, the HRP labelling studies of the previously lesioned L5 root show many fibers and terminals with boutons in their proper positions of laminal 2 and 3 within the doral horn. The exact relationship of the incoming fibers with the implant surface and the presence of a number of novel terminal arbor malformations in a sub-population of the axons provides convincing evidence that the fibers in the cord are truly regenerated.

Moreover, six (6) of the nineteen (19) rats implanted with the pennant-shaped nitrocellulose implants coated with activated immature rat astrocytes exhibited functional recovery of many of their basic sensory motor behaviors approximately 5 to 7 days following insertion of the implants. Hence, the above results demonstrate that activated immature astrocytes seeded onto specially designed nitrocellulose implants promote directed axonal and blood vessel regeneration and repress glial scar formation in the spinal cord.

EXAMPLE 3

Immortalization of the Activated Immature Astrocytes

The purified activated immature (embryonic through postnatal day 8) astrocytes produced according to the process set forth in Example 2 were immortalized with defective retrovirus coding for SV40 T antigen and bacterial neomycin resistance genes by the following procedure. The purified activated immature astrocytes were seeded on to a $5 \times 10^5/60$ mm dish on day 1. On day 2 the medium was replaced with 2 ml of the viral supernatant containing the defective retrovirus coding for SV40T antigen and bacterial neomycin resistance genes. (Obtained from Dr. P. S. Jak, University College at London, London, England). The cells were incubated for 2–3 hours and then the fiber was removed and fresh medium was resupplied. Neomycin resistant colonies were selected with medium containing G418 (a neomycin analog obtained from Gibco, Grand Island, N.Y.). Colonies which displayed normal phenotype in culture, i.e. astrocyte morphology and contact inhibition of growth, were selected and cultured over a period of months and passages without undergoing microscopically observable change. The clones were then stained for glial fibrilliary protein and tested for promotion of axonal growth. The clones were GFAP-positive and promoted axonal growth.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims and the equivalents thereof.

What we claim is:

1. A method for promoting directed axon regeneration which comprises the steps of:
    (a) providing activated immature astrocytes;
    (b) seeding an effective amount of said activated immature astrocytes on to an implant; and,
    (c) inserting said seeded implant near the ends of damaged axons to promote directed axon regeneration.

2. The method of claim 1, wherein said activated immature astrocytes are stellate-shaped, GFAP-positive astrocytes.

3. The method of claim 1, wherein said activated immature astrocytes are embryonic through postnatal day 8 astrocytes.

4. The method of claim 3, wherein said activated immature astrocytes are postnatal day 2 through postnatal day 8 astrocytes.

5. The method of claim 1, wherein said damaged axons are forebrain axons.

6. The method of claim 5, wherein said forebrain axons are commissural axons.

7. The method of claim 1, wherein said damaged axons are spinal axons.

8. The method of claim 7, wherein said spinal axons are sensory axons.

9. The method of claim 1, wherein said implant is nitrocellulose filter paper.

10. The method of claim 9, wherein said nitrocellulose filter paper has a pore size of about 0.45 um.

11. The method of claim 9, wherein said nitrocellulose filter paper has a pore size of about 8.0 um.

12. The method of claim 10, wherein said 0.45 um pore size nitrocellulose filter paper is a 1-mm$^2$ homeplate shaped piece of filter paper.

13. The method of claim 11, wherein said 8.0 um pore size nitrocellulose filter paper is a pennant-shaped piece of filter paper.

14. The method of claim 13, wherein said pennant-shaped piece of filter paper is about 3 mm$\times$.75 mm$\times$250 um.

15. A method for promoting directed axon regeneration in an animal lacking activated immature astrocytes which comprises the steps of:
    (a) providing activated immature astrocytes;
    (b) seeding an effective amount of said activated immature astrocytes on to an implant; and,
    (c) inserting said seeded implant into damaged axons of an animal lacking activated immature astrocytes to promote directed axon regeneration.

16. The method of claim 15, wherein said activated immature astrocytes are stellate-shaped, GFAP-positive astrocytes.

17. The method of claim 15, wherein said activated immature astrocytes are embryonic through postnatal day 8 astrocytes.

18. The method of claim 17, wherein said activated immature astrocytes are postnatal day 2 through postnatal day 8 astrocytes.

19. The method of claim 15, wherein said damaged axons are forebrain axons.

20. The method of claim 19, wherein said forebrain axons are commissural axons.

21. The method of claim 15, wherein said damaged axons are spinal axons.

22. The method of claim 21, wherein said spinal axons are sensory axons.

23. The method of claim 15, wherein said animal lacking activated immature astrocytes is an animal 14 days old or older.

24. The method of claim 15, wherein said implant is nitrocellulose filter paper.

25. The method of claim 24, wherein said nitrocellulose filter paper has a pore size of about 0.45 um.

26. The method of claim 25, wherein said 0.45 um pore size nitrocellulose filter paper is a 1-mm² home-plate shaped piece of filter paper.

27. The method of claim 24, wherein said nitrocellulose filter paper has a pore size of about 8.0 um.

28. The method of claim 27, wherein said 8.0 mm pore size nitrocellulose filter paper is a pennant-shaped piece of filter paper.

29. The method of claim 28, wherein said pennant-shaped piece of filter paper is about 3 mm.×0.75 mm.×250 um.

30. A method for reducing glial scar formation in damaged central nervous system tissue comprising the steps of:
(a) providing activated immature astrocytes;
(b) seeding an effective amount of said activated immature astrocytes on to an implant; and,
(c) inserting said seeded implant into damaged tissue of the central nervous system to reduce glial scar formation.

31. The method of claim 30, wherein said activated immature astrocytes are stellate-shaped, GFAP-positive astrocytes.

32. The method of claim 30, wherein said activated immature astrocytes are embryonic through postnatal day 8 astrocytes.

33. The method of claim 32, wherein said activated immature astrocytes are postnatal day 2 through postnatal day 8 astrocytes.

34. The method of claim 30, wherein said damaged tissue of the central nervous system is a forebrain axon.

35. The method of claim 34, wherein said forebrain axon is a commissural axon.

36. The method of claim 30, wherein said damaged tissue of the central nervous system is a spinal axon.

37. The method of claim 36, wherein said spinal axon is a sensory axon.

38. The method of claim 30, wherein said implant is nitrocellulose filter paper.

39. The method of claim 38, wherein said nitrocellulose filter paper has a pore size of about 0.45 um.

40. The method of claim 39, wherein said 0.45 um pore size nitrocellulose filter paper is a 1-mm² home-plate shaped piece of filter paper.

41. The method of claim 38, wherein said nitrocellulose paper has a pore size of about 8.0 um.

42. The method of claim 41, wherein said 8.0 um pore size nitrocellulose filter paper is a pennant-shaped piece of filter paper.

43. A method for reducing glial scar formation in damaged central nervous system tissue in an animal lacking activated immature astrocytes which comprises the steps of:
(a) providing activated immature astrocytes;
(b) seeding an effective amount of said activated immature astrocytes on to an implant; and,
(c) inserting said seeded implant into damaged tissue of the central nervous system of an animal lacking activated immature astrocytes to reduce glial scar formation.

44. The method of claim 43, wherein said activated immature astrocytes are stellate-shaped, GFAP-positive astrocytes.

45. The method of claim 43, wherein said activated immature astrocytes are embryonic through postnatal day 8 astrocytes.

46. The method of claim 45, wherein said activated immature astrocytes are postnatal day 2 through postnatal day 8 astrocytes.

47. The method of claim 43, wherein said damaged tissue of the central nervous system is a forebrain axon.

48. The method of claim 47, wherein said forebrain axon is a commissural axons.

49. The method of claim 43, wherein said damaged tissue of the central nervous system is a spinal axon.

50. The method of claim 49, wherein said spinal axon is a sensory axon.

51. The method of claim 43, wherein said animal lacking activated immature astrocytes is an animal 14 days old or older.

52. The method of claim 43, wherein said implant is nitrocellulose filter paper.

53. The method of claim 52, wherein said nitrocellulose filter paper has a pore size of about 0.45 um.

54. The method of claim 53, wherein said 0.45 um pore size nitrocellulose filter paper is a 1-mm² home-plate shaped piece of filter paper.

55. The method of claim 52, wherein said nitrocellulose filter paper has a pore size of about 8.0 um.

56. The method of claim 55, wherein said 8.0 um pore size nitrocellulose filter paper is a pennant-shaped piece of filter paper.

57. The method of claim 56, wherein said pennant-shaped piece of filter paper is about 3 mm.×0.75 mm.×250 um.

* * * * *